United States Patent
Kang et al.

(10) Patent No.: US 10,934,164 B2
(45) Date of Patent: Mar. 2, 2021

(54) LIQUID HYDROGEN STORAGE MATERIAL

(71) Applicant: Korea University Research and Business Foundation, Seoul (KR)

(72) Inventors: Jeongwon Kang, Seoul (KR); Wonsik Han, Namyangju-si (KR); Byeongsoo Shin, Seoul (KR); Joori Jung, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 36 days.

(21) Appl. No.: 16/193,627

(22) Filed: Nov. 16, 2018

(65) Prior Publication Data

US 2019/0152775 A1    May 23, 2019

(30) Foreign Application Priority Data

Nov. 23, 2017  (KR) ........................ 10-2017-0157088

(51) Int. Cl.
| | | |
|---|---|---|
| *C01B 3/00* | (2006.01) | |
| *B01J 23/46* | (2006.01) | |
| *B01J 21/18* | (2006.01) | |
| *C07C 5/367* | (2006.01) | |
| *C07C 15/14* | (2006.01) | |
| *B01J 23/44* | (2006.01) | |
| *B01J 23/42* | (2006.01) | |
| *C07C 5/10* | (2006.01) | |
| *B01J 21/04* | (2006.01) | |

(52) U.S. Cl.
CPC ............ *C01B 3/0015* (2013.01); *B01J 21/04* (2013.01); *B01J 21/18* (2013.01); *B01J 23/42* (2013.01); *B01J 23/44* (2013.01); *B01J 23/462* (2013.01); *C07C 5/10* (2013.01); *C07C 5/367* (2013.01); *C07C 15/14* (2013.01); *C07C 2521/04* (2013.01); *C07C 2521/18* (2013.01); *C07C 2523/42* (2013.01); *C07C 2523/44* (2013.01); *C07C 2523/46* (2013.01); *C07C 2601/14* (2017.05)

(58) Field of Classification Search
None
See application file for complete search history.

(56) References Cited

U.S. PATENT DOCUMENTS 7,429,372 B2   9/2008   Pez et al.

FOREIGN PATENT DOCUMENTS

| | | |
|---|---|---|
| JP | 10-194701 A | 7/1998 |
| JP | 2002-274801 A | 9/2002 |
| JP | 4907210 B2 | 3/2012 |
| KR | 10-0870528 B1 | 11/2008 |
| KR | 10-0992911 B1 | 11/2010 |
| KR | 10-1001946 B1 | 12/2010 |
| KR | 10-2015-0097558 A | 8/2015 |
| WO | WO 2016/110215 A1 | 7/2016 |

OTHER PUBLICATIONS

Han, Da Jung, et al., "A Novel Eutectic Mixture of Biphenyl and Diphenylmethane as a Potential Liquid Organic Hydrogen Carrier: Catalytic Hydrogenation", *Energy Technology* (9 pages in English).

*Primary Examiner* — Tanisha Diggs
(74) *Attorney, Agent, or Firm* — NSIP Law

(57) ABSTRACT

Disclosed is a liquid hydrogen storage material, and more particularly, a hydrogen storage material which contains m-phenyltoluene (m=2, 3) and undergoes reversible dehydrogenation/hydrogenation reactions or contains a binary eutectic mixture or a ternary eutectic mixture of m-phenyltoluene (m=2, 3, 4).

2 Claims, 10 Drawing Sheets

LIQUID HYDROGEN STORAGE MATERIAL

CROSS-REFERENCE TO RELATED APPLICATIONS

This application claims priority under 35 U.S.C. § 119 to Korean Patent Application No. 10-2017-0157088 filed on Nov. 23, 2017, in the Korean Intellectual Property Office, the disclosures of which are incorporated by reference herein in their entireties.

BACKGROUND

Embodiments of the inventive concept described herein relate to a liquid hydrogen storage material, and more particularly, to a liquid hydrogen storage material which undergoes reversible dehydrogenation/hydrogenation reactions.

Recently, hydrogen energy has attracted attention as eco-friendly alternative energy since environmental problems such as global warming due to the emission of carbon dioxide and energy problems such as depletion of petroleum resources have come to the fore. It has become important to develop a technology to store and transport hydrogen safely and efficiently for the practical use of hydrogen energy. There are various methods of storing hydrogen, but a method using a hydrogen storage material capable of reversibly storing and releasing hydrogen is expected as a hydrogen storage medium to be mounted on a fuel cell vehicle.

As hydrogen storage materials, carbon materials such as activated carbon, fullerene, and nanotubes and hydrogen storage alloys such as $LaNi_5$ and TiFe are known. Among these, hydrogen storage alloys are preferred as a hydrogen storage material for storing and transporting hydrogen since the hydrogen storage alloys have a higher hydrogen density per unit volume than carbon materials. However, there is a problem that it is difficult to secure the resources and the cost thereof is high since the hydrogen storage alloys such as $LaNi_5$ and TiFe contain rare metals such as La, Ni, and Ti. In addition, there is a problem that a significantly heavy alloy is required in order to store a large amount of hydrogen since the weight of the alloy itself is great in the case of conventional hydrogen storage alloys.

In addition to these hydrogen storage alloys, N-ethylcarbazole (NEC) to be used as an organic compound hydrogen storage material has a melting point of 68° C., which means that NEC is solid at normal temperature, and it is thus difficult to apply NEC to the existing infrastructures.

In addition, biphenyl has a hydrogen storage capacity of 7.2 wt % to be relatively higher than that of NEC and can be thus used for reversible hydrogen storage, but biphenyl has inadequate physical properties as a reversible liquid hydrogen storage material since it has a boiling point of 225° C. and is solid at normal temperature.

In addition, a liquid organic hydrogen carrier (LOHC), which is used as a liquid hydrogen storage material and uses an organic compound, has a higher weight or volume storage density than compressed hydrogen and an advantage that the infrastructure investment is minimized since the existing petroleum storage system can be utilized for the LOHC as it is. In addition, it is possible to construct a high efficiency system as compared with other processes if the reversibility of the hydrogenation/dehydrogenation reactions of LOHC is secured, and it is thus possible to make a breakthrough in hydrogen energy field.

Toluene and dibenzyl-toluene of cyclic hydrocarbons are each used in Japan and Germany as LOHC to commercialize hydrogen energy, and in the US, the Department of Energy (DOE) is leading studies using boron-nitrogen-containing amine-borane-based materials and N-ethylcarbazole as LOHC candidates.

Toluene and dibenzyl-toluene are inefficient in terms of thermodynamics as compared with other materials since a high temperature of 300° C. or more is required for the dehydrogenation reaction thereof. On the contrary, amine-borane, which is a material containing binary elements such as B and N, easily undergoes the dehydrogenation reaction even at a low temperature (up to 80° C.) and a has a hydrogen storage capacity (hydrogen mass with respect to hydrogenated storage material mass) of 5 wt % or more but has a disadvantage that the hydrogenation/dehydrogenation reactions are irreversible.

N-ethylcarbazole has been regarded as the most promising liquid organic hydrogen carrier (LOHC) and long been subjected to the studies by American AIR PRODUCTS, and it has been confirmed that the dehydrogenation reaction of N-ethylcarbazole can take place even at a temperature (up to 180° C.) lower than that for the dehydrogenation reaction of a hydrocarbon material because of the presence of a heteroatom (N) in the molecule. In addition, N-ethylcarbazole is attracting great attention since the hydrogenation/dehydrogenation reactions thereof can reversibly take place. However, 5.8 wt % of the hydrogen storage capacity (hydrogen mass with respect to material mass: kg $H_2$/kg material) of N-ethylcarbazole is lower than 6.5 wt % of the target hydrogen storage capacity (hydrogen mass with respect to system mass: kg $H_2$/kg system; "system" is a concept including the tank, the storage material, the valve, and the like) set by US DOE.

In addition, N-ethylcarbazole has a disadvantage of being present as a solid at normal temperature since the melting point of the dehydrogenated form (N-ethylcarbazole) is 68° C.

Hence, it has been demanded to develop a liquid hydrogen storage material which has a high hydrogen storage capacity, can undergo reversible dehydrogenation/hydrogenation reactions, and can be present as a liquid even at a low temperature.

Patent Document 1: Korean Patent No. 1001946
Patent Document 2: Korean Patent No. 0870528
Patent Document 3: U.S. Pat. No. 10,833,484

SUMMARY

Embodiments of the inventive concept provide a material having suitable physical properties as a reversible liquid hydrogen storage material.

Embodiments of the inventive concept also provide a liquid hydrogen storage material capable of being hydrogenated/dehydrogenated even with a small amount of heat since hydrogen storage materials such as toluene, benzene, and dibenzyl-toluene can be present as a liquid at normal temperature and normal pressure and can reversibly store and release hydrogen but have a disadvantage of thermodynamically requiring a large amount of heat when releasing hydrogen.

According to an exemplary embodiment, a liquid hydrogen storage material contains m-phenyltoluene (m=2, 3) and undergoes reversible dehydrogenation/hydrogenation reactions.

According to an exemplary embodiment, in the liquid hydrogen storage material, either of $Ru/Al_2O_3$ or Ru/C is used as a hydrogenation catalyst in a hydrogenation reaction.

According to an exemplary embodiment, in the liquid hydrogen storage material, the hydrogenation reaction takes place at from 150° C. to 180° C.

According to an exemplary embodiment, in the liquid hydrogen storage material, any one of Pd/C, Pd/Al$_2$O$_3$, Pt/C or Pt/Al$_2$O$_3$ is used as a dehydrogenation catalyst in a dehydrogenation reaction.

According to an exemplary embodiment, a liquid hydrogen storage material contains a binary eutectic mixture or a ternary eutectic mixture of m-phenyltoluene (m=2, 3, 4).

According to an exemplary embodiment, in the liquid hydrogen storage material, a eutectic mixture of 2-phenyltoluene and 3-phenyltoluene among binary eutectic mixtures has a molar ratio of 2-phenyltoluene: 3-phenyltoluene=0.001 to 0.999:0.999 to 0.001.

According to an exemplary embodiment, in the liquid hydrogen storage material, a eutectic mixture of 2-phenyltoluene and 4-phenyltoluene among binary eutectic mixtures has a molar ratio of 2-phenyltoluene:4-phenyltoluene=0.6 to 0.999:0.4 to 0.001.

According to an exemplary embodiment, in the liquid hydrogen storage material, wherein a eutectic mixture of 3-phenyltoluene and 4-phenyltoluene among binary eutectic mixtures has a molar ratio of 3-phenyltoluene:4-phenyltoluene=0.6 to 0.999:0.4 to 0.001.

According to an exemplary embodiment, in the liquid hydrogen storage material, a ternary eutectic mixture has a molar ratio of 2-phenyltoluene:3-phenyltoluene:4-phenyltoluene=a:b:c (where a+b+c=1, a>0, b>0, and c<0.4).

The liquid hydrogen storage material according to the inventive concept is present as a liquid at room temperature and can be reversibly hydrogenated and dehydrogenated by adding a catalyst thereto and raising the temperature thereof.

In addition, the liquid hydrogen storage material according to the inventive concept can be hydrogenated/dehydrogenated even with a small amount of heat.

In addition, the liquid hydrogen storage material according to the inventive concept is present in a liquid state at normal temperature and normal pressure after hydrogen storage and can be thus transported through a pipe. Particularly, the liquid hydrogen storage material can maintain the liquid state even at a low temperature of −28.85° C. and can be thus used as a liquid hydrogen storage material even in cold regions (Siberia, polar regions). In addition, the hydrogen storage capacity of the liquid hydrogen storage material of the inventive concept is 6.7 wt %, which meets the DOE standard, and the hydrogen storage material is also advantageous in terms of energy since it can release hydrogen even at 250° C. while conventional hydrocarbon materials require a high temperature of 300° C. or more.

In addition, the inventive concept can lead to the development of industries connected with the national power network and contribute to the new energy industry as commercialization of hydrogen fuel cell vehicles, supply of hydrogen stations and development of high-capacity energy storage technologies will be accelerated through practical use of the hydrogen storage and transportation technologies using liquid compounds and liquid compounds are used as new and renewable energy-linked high-capacity energy storage (ESS) media.

BRIEF DESCRIPTION OF THE FIGURES

The above and other objects and features of the inventive concept will become apparent by describing in detail exemplary embodiments thereof with reference to the accompanying drawings.

DETAILED DESCRIPTION

Below, the inventive concept will be more fully described with reference to accompanying drawings. First, it should be noted that the same component or part in drawings indicates the same reference marks/numeral so far as possible. In describing the inventive concept, the detailed description associated with a related known function or configuration is omitted to avoid the ambiguousness of the inventive concept.

In the specification, the terms used to express the degree, such as "approximately", "about", and "substantially", may be used as a meaning approximate to a numeral value when fabrication and material tolerance inherent to a mentioned meaning is suggested, and may be used to prevent an infringer from unconscientiously using the present disclosure in which an exact or absolute numerical value is mentioned for better understanding of the inventive concept.

Embodiments of the inventive concept described herein relate to a liquid hydrogen storage material containing m-phenyltoluene (m=2, 3).

2-phenyltoluene (2-PT) and 3-phenyltoluene (3-PT) are present as a liquid substance at room temperature (25° C.). In other words, 2-phenyltoluene (2-PT) and 3-phenyltoluene (3-PT) are present as a liquid at room temperature as the melting point of 2-phenyltoluene (2-PT) is 0° C. and the melting point of 3-phenyltoluene (3-PT) is from 4 to 5° C.

In addition, 2-phenyltoluene (2-PT) and 3-phenyltoluene (3-PT) maintain the liquid state even at a high temperature as the boiling point of 2-phenyltoluene (2-PT) is 255° C. and the boiling point of 3-phenyltoluene (3-PT) is 272° C., and it can be thus seen that the temperature range in which these can store hydrogen is wide.

The m-phenyltoluene (m=2, 3), which is a hydrogen storage material of the inventive concept, can store hydrogen through hydrogenation, and the m-phenyltoluene (m=2, 3) can undergo reversible dehydrogenation/hydrogenation reactions.

The hydrogenation/dehydrogenation reactions of m-phenyltoluene (m=2, 3) can reversibly take place as follows.

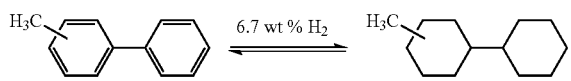

The hydrogen weight capacity can be 6.7 wt % when m-phenyltoluene (m=2, 3) is hydrogenated, and this is a higher hydrogen storage capacity than 5.8 wt % of NEC (N-ethylcarbazole) to be used as a conventional hydrogen storage material.

Figure 1:
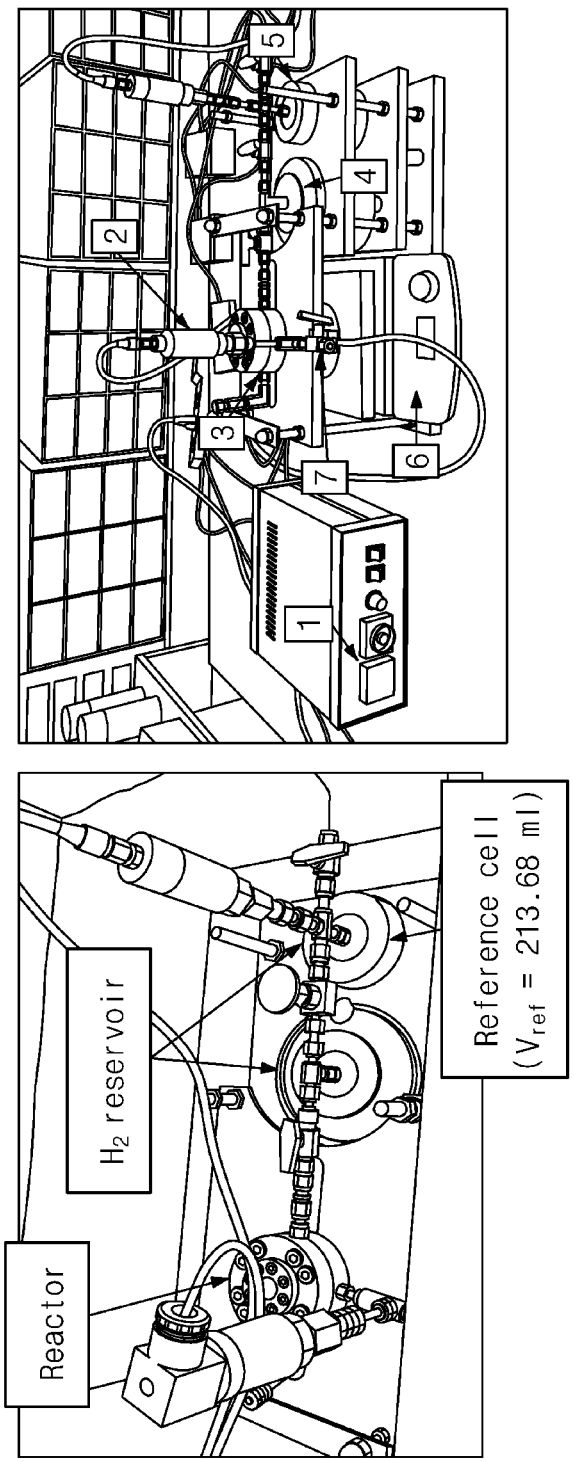
FIG. 1 illustrates an apparatus for conducting a hydrogenation reaction to hydrogenate the hydrogen storage material of the inventive concept and measuring the hydrogen storage capacity.

FIG. 1 illustrates an apparatus for conducting a hydrogenation reaction to hydrogenate the hydrogen storage material of the inventive concept and measuring the hydrogen storage capacity.

The hydrogenation reaction takes place by introducing m-phenyltoluene (m=2, 3), a catalyst and $H_2$ into the reactor.

A catalyst is required in the hydrogenation reaction, and either of $Ru/Al_2O_3$ or Ru/C may be used as the hydrogenation catalyst. A ruthenium-based catalyst may be utilized as the hydrogenation catalyst.

In addition, the hydrogenation reaction using the hydrogen storage material of the inventive concept takes place at from 50 to 70 bar and from 150° C. to 180° C.

In addition, the amount of the hydrogenation catalyst to be introduced into the reactor is preferably from 10 to 20 wt % of the mass (g) of m-phenyltoluene (m=2, 3) of the reactant.

The hydrogen weight capacity to be stored using the hydrogen storage material of the inventive concept is 6.7 wt %, and this can be measured by using a hydrogen storage capacity measuring apparatus.

The apparatus for conducting the hydrogenation reaction and measuring the hydrogen storage capacity may be equipped with 1) a temperature controller of a heating mantle, 2) a pressure gauge, 3) a reactor, 4) and 5) a hydrogen storage vessel, 6) a stirrer, and 7) a heating mantle.

The temperature of 7) the heating mantle can be controlled by using 1) the temperature controller of the heating mantle. The heating mantle surrounds 3) the reactor, and the reaction can be conducted by raising the temperature to the desired temperature. 2) The pressure gauge measures the pressure of hydrogen in the reactor, and the hydrogen pressure decreases as the reaction takes place since the reaction is a hydrogenation reaction. It can be judged that the reaction has been completed when the pressure does not change any more.

The measurement of hydrogen mass is conducted utilizing the principle of measuring the mass of hydrogen reacted in the reactor by the hydrogen pressure difference in the hydrogen storage vessel (reference cell).

The volume of 5) the hydrogen storage vessel (reference cell) can be accurately measured by the mass difference of liquefied carbon dioxide. In the experiment of the inventive concept, the volume of 5) the hydrogen storage vessel (reference cell) was 213.68 mL. ($V_{ref}$=213.68 mL)

In the inventive concept, the experiment of hydrogenation reaction is conducted as follows.

m-phenyltoluene (m=2, 3) of the reactant, a catalyst and $H_2$ are injected into the reactor, then the pressure ($P_{reac,1}$) in the reactor is set to 70 bar in a constant-temperature water bath (20° C.), and the pressure ($P_{ref}$) in the reference cell is set to 100 bar and stabilized.

Thereafter, the reactor is taken out from the constant-temperature water bath and then heated to from 150° C. to 180° C. by using a heating jacket, and the hydrogenation reaction is conducted.

After the reaction is terminated, the pressure ($P_{reac,2}$) in the reactor is stabilized in a constant-temperature water bath (20° C.).

Thereafter, the hydrogen in the reference cell is injected into the reactor by using the metering valve, and the pressure in the reactor after the reaction is adjusted to $P_{reac,1}$ of the pressure before the reaction ($P_{reac,2} \rightarrow P_{reac,1}$).

The mass of hydrogen can be determined by measuring the pressure ($P_{reac,2}$) in the reactor after the reaction and calculating the amount of hydrogen reacted in the reactor using Equation (1).

$$m_{H_2} = [\rho_{H_3}(T, P_{ref,1}) - \rho_{H_2}(T, P_{ref,2})] \times V_{ref} \qquad \text{Equation 1}$$

ρ: density of hydrogen, $P_{ref,1}$: hydrogen pressure in 5) hydrogen storage vessel (before reaction), $P_{ref,2}$: hydrogen pressure in 5) hydrogen storage vessel (after reaction), $V_{ref}$: volume of 5) hydrogen storage vessel (213.68 ml)

(Here, the hydrogen density data required for calculation of hydrogen mass refer to NIST TRC data)

Figure 2:
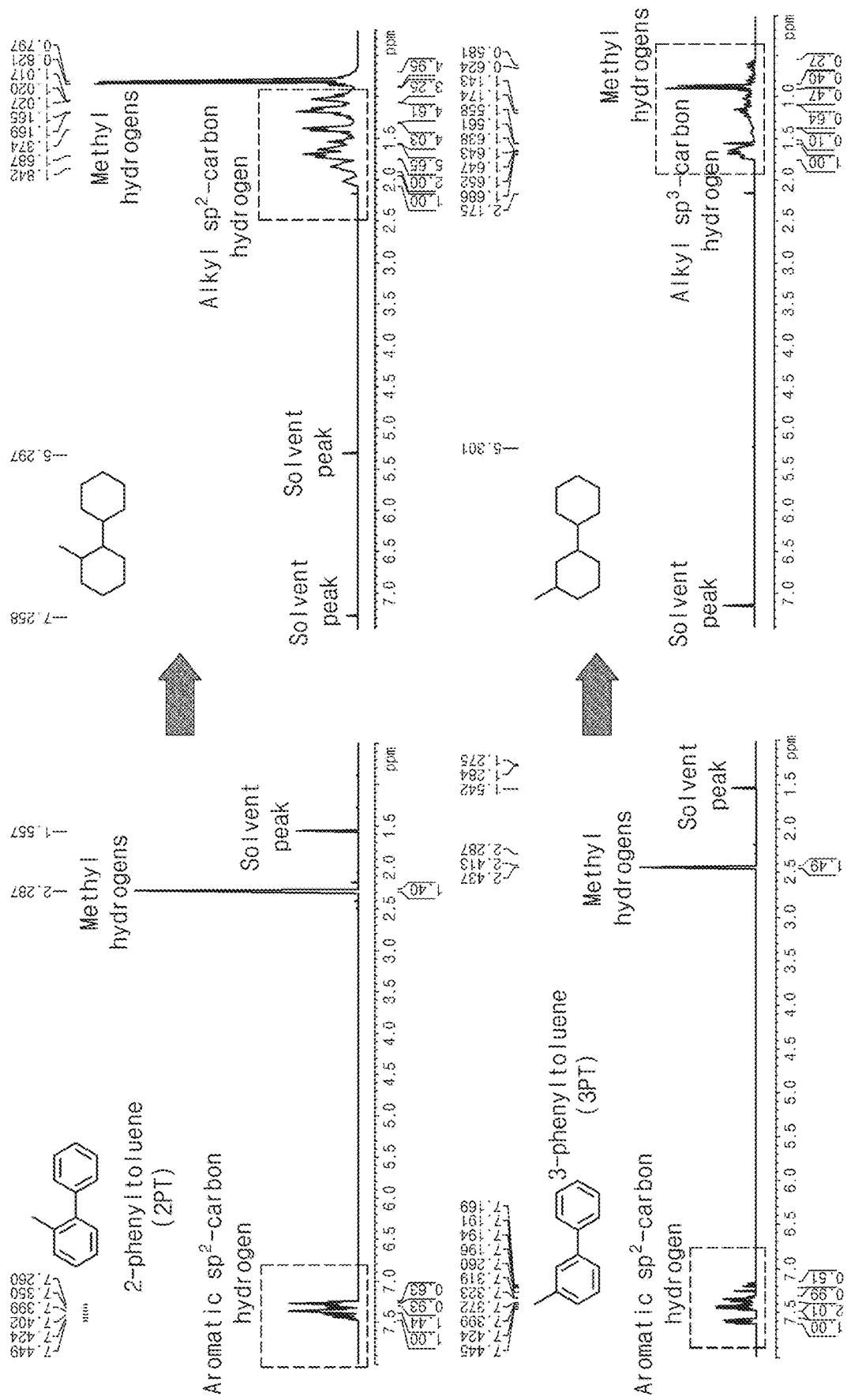
FIG. 2 illustrates the results for $^1$H NMR analysis conducted after hydrogenation of the hydrogen storage material according to an embodiment of the inventive concept.

FIG. 2 illustrates the results for $^1$H NMR analysis conducted after hydrogenation of the hydrogen storage material according to an embodiment of the inventive concept.

FIG. 2 illustrates the results for $^1$H NMR analysis conducted after 5 g of 2-phenyltoluene (2-PT) and 5 g of 3-phenyltoluene (3-PT) are hydrogenated using 0.5 g of $Ru/Al_2O_3$ as a catalyst at 160° C.

As illustrated in FIG. 2, it is confirmed that complete hydrogenation takes place since the proton (H) peaks attributed to sp2-carbon of the aromatic ring at between 7 and 8 ppm all disappear and the peaks attributed to sp3-carbon newly appear at between 0 and 2.5 ppm through $^1$H NMR analysis conducted after the hydrogenation reaction.

The capacity at which hydrogen is stored after the hydrogenation has completely proceeded is 6.7 wt % of an ideal capacity.

These results are presented in the following Table 1.

TABLE 1

| Material | Catalyst | Reaction condition | Feed(g) material/catalyst | Ideal wt % | Experimental wt % |
|---|---|---|---|---|---|
| 2-phenyltoluene | Ru/Al$_2$O$_3$ | 160° C./30 min | 5/0.5 | 6.7 wt % | Confirmed that material is completely hydrogenated through NMR analysis |
| 3-phenyltoluene | Ru/Al$_2$O$_3$ | 160° C./30 min | 5/0.5 | 6.7 wt % | Confirmed that material is completely hydrogenated through NMR analysis |

In addition, the hydrogen storage material of the inventive concept can be dehydrogenated when it is hydrogenated, and the dehydrogenation reaction can take place as a reverse reaction in the reaction formula since a reversible reaction is possible.

Figure 3:
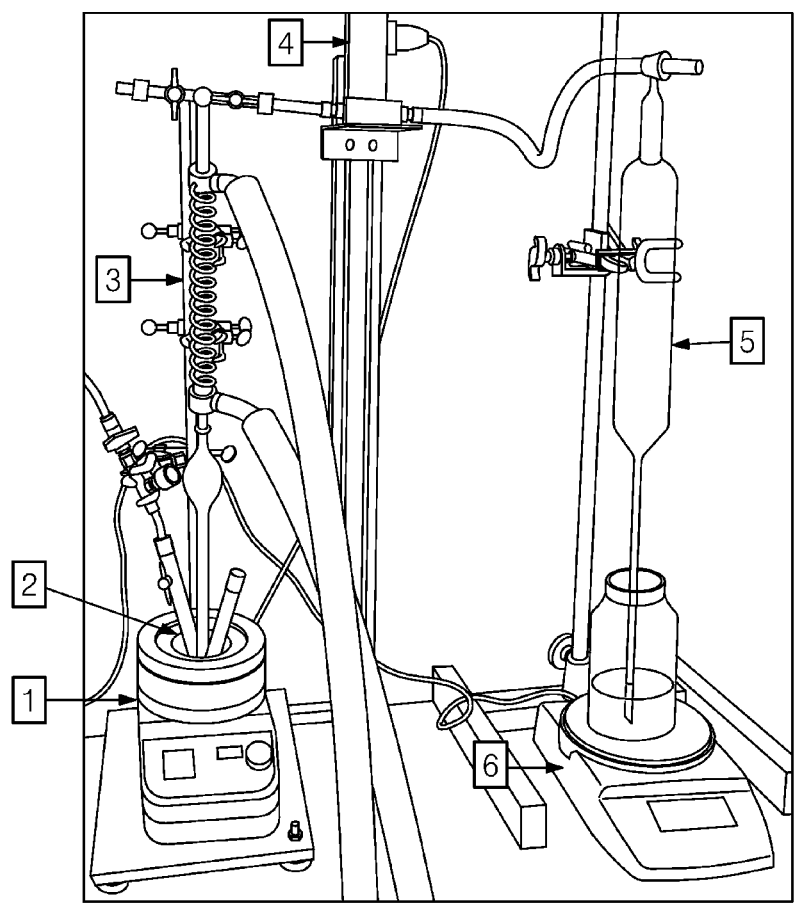
FIG. 3 illustrates a dehydrogenation reaction apparatus for dehydrogenating a hydrogenated hydrogen storage material.

FIG. 3 illustrates a dehydrogenation reaction apparatus for dehydrogenating a hydrogenated hydrogen storage material.

Referring to FIG. 3, the dehydrogenation reaction apparatus is equipped with 1) a heating mantle, 2) a batch reactor, 3) a condenser, 4) a MFM, 5) an oil burette, and 6) a mass measuring device.

When the dehydrogenation reaction takes place, the signals from the MFM and the mass measuring apparatus can be monitored in real time by using a computer to measure the hydrogen release rate. The mass of the oil from the oil burette is compared when a fixed amount of hydrogen is injected into the reactor in order to enhance the accuracy of quantitative measurement of hydrogen to be released in this manner.

The dehydrogenation reaction is conducted as follows: the dehydrogenation reaction takes place and hydrogen is released when the hydrogenated material and the catalyst are introduced into 2) the reactor and the temperature thereof is raised. The release rate of hydrogen can be measured by using the MFM or oil burette and the mass measuring apparatus. The released hydrogen passes through 3) the condenser and 4) the MFM and pushes the oil in 5) the oil burette into the glass bottle on 6) the mass measuring apparatus. The oil pushed out changes the weight of the glass bottle on the mass measuring apparatus and this mass change can be measured in real time by using a computer. The total amount of hydrogen released during the dehydrogenation reaction can be obtained through such a mass measurement.

The mass is measured using the oil pushed out, but this mass value does not match the amount of hydrogen released (volume of hydrogen: ml). The exact amount of hydrogen can be determined by 'calibration' in order to confirm the correlation between the mass of the oil pushed out and the amount of hydrogen released (ml).

In other words, the same condition as when the reaction actually takes place is maintained in a state (empty state) in which the catalyst and the reactant are not present in the reactor, a fixed amount of hydrogen is injected into the reactor, and the value indicated on the mass measuring apparatus is confirmed after the injection is completed. The correlation between the amount of hydrogen injected and the mass value measured using oil is confirmed through this. The mass value measured in the experiment of dehydrogenation reaction can be calibrated through this and the amount of hydrogen released can be accurately measured.

In the dehydrogenation reaction, any one of Pd/C, Pd/Al$_2$O$_3$, Pt/C or Pt/Al$_2$O$_3$ may be used as the dehydrogenation catalyst. In the dehydrogenation reaction, palladium or a platinum-based catalyst is used.

It is preferable that the dehydrogenation catalyst is contained at from 10 to 20 wt % of the material to be introduced into the reactor.

In the dehydrogenation reaction, it is preferable that the reaction temperature is set to from 250° C. to 350° C.

Figure 4:
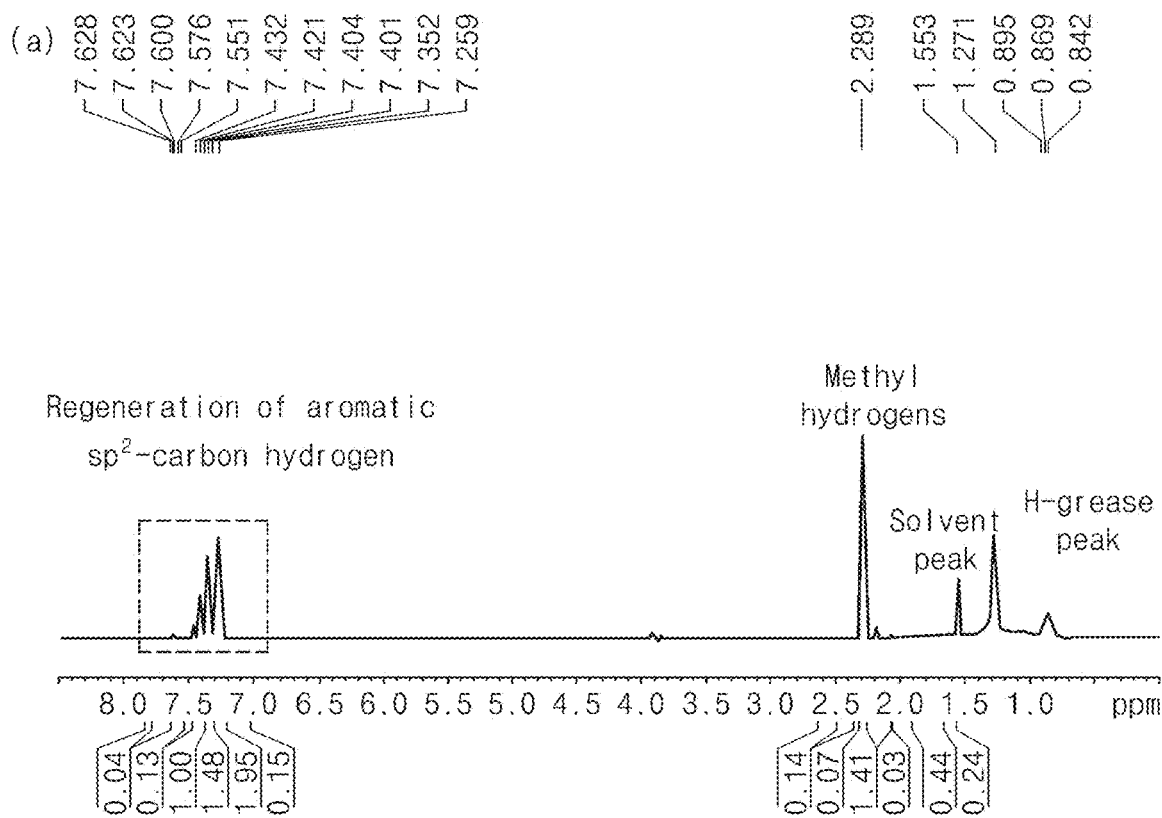
FIG. 4 illustrates (a) the results for $^1$H NMR analysis conducted after the dehydrogenation reaction of 2-phenyltoluene, which is a hydrogen storage material of the inventive concept, and (b) the results for the dehydrogenation reaction of 2-phenyltoluene with time.
Figure 4:
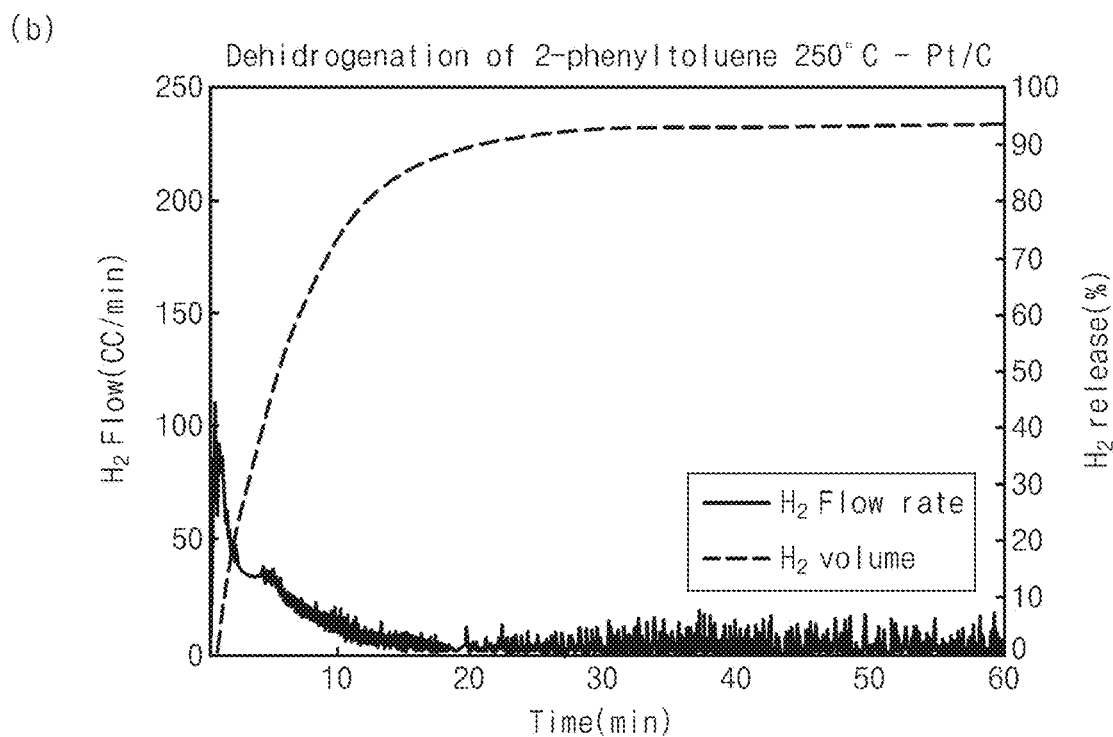

FIG. 4 illustrates (a) the results for $^1$H NMR analysis conducted after the dehydrogenation reaction of 2-phenyltoluene, which is a hydrogen storage material of the inventive concept, and (b) the results for the dehydrogenation reaction of 2-phenyltoluene with time.

In FIG. 4, the dehydrogenation reaction of hydrogenated 2-phenyltoluene (2-PT) is conducted at 250° C. for about 60 minutes using Pd/C as a dehydrogenation catalyst.

Referring to (a) of FIG. 4, it is confirmed that the dehydrogenation reaction qualitatively takes place by confirming that the proton (H) peaks attributed to sp2-carbon of the aromatic ring appear again at between 7 and 8 ppm and, at the same time, the proton peaks attributed to the methyl group shift to 2.28 ppm of the original position through $^1$H NMR analysis of dehydrogenated 2-phenyltoluene (2-PT).

In addition, in (b) of FIG. 4, the black line in the graph indicates the hydrogen release rate measured by using MFM and the red line indicates the total amount of hydrogen determined by calibrating the mass measured by using the mass measuring apparatus. The percentage means the calibrated volume value of released hydrogen measured in an experiment with respect to the total amount of hydrogen (theoretical hydrogen volume) that can be released from 5 g of reaction sample, and 100% means that hydrogen in the reactant is completely dehydrogenated.

It can be seen that 90% or more of the theoretical dehydrogenation amount is dehydrogenated when 30 minutes elapses from the start of dehydrogenation through this.

Meanwhile, in the inventive concept, eutectic mixtures in which two or three m-phenyltoluenes (m=2, 3, 4) are mixed can be utilized as a hydrogen storage material.

The melting points of 2-phenyltoluene, 3-phenyltoluene and 4-phenyltoluene are 0° C., from 4 to 5° C. and from 44 to 47° C., respectively, as presented in the following Table 2.

TABLE 2

| Constituent material | Constitutional formula | Hydrogen storage capacity (wt %) | Melting point (° C.) |
| --- | --- | --- | --- |
| 2-phenyltoluene | | 6.7 | 0 |
| 3-phenyltoluene | | 6.7 | 4 to 5 |
| 4-phenyltoluene | | 6.7 | 44 to 47 |

The eutectic mixture can maintain the liquid state at room temperature when these two materials or three materials are appropriately mixed.

A hydrogen storage material can be prepared by a binary system in which two materials are mixed.

Hydrogen storage materials can be prepared by mixing (1) 2-phenyltoluene and 3-phenyltoluene, (2) 2-phenyltoluene and 4-phenyltoluene, and (3) 3-phenyltoluene and 4-phenyltoluene.

First, among the binary eutectic mixtures, it is preferable that the molar ratio of 2-phenyltoluene to 3-phenyltoluene is 0.001 to 0.999:0.999 to 0.001. The eutectic mixture of 2-phenyltoluene and 3-phenyltoluene can maintain the liquid state at normal temperature even though these are mixed in all molar ratio ranges.

In addition, it is most preferable that the molar ratio of 2-phenyltoluene to 3-phenyltoluene is 0.53:0.47, and the eutectic point at this time is −24.25° C. and the eutectic mixture can maintain the liquid state at a significantly low temperature.

In addition, among the binary eutectic mixtures, it is preferable that the molar ratio of 2-phenyltoluene to 4-phenyltoluene is 0.6 to 0.999:0.4 to 0.001. The eutectic mixture of 2-phenyltoluene and 4-phenyltoluene maintains the liquid state at normal temperature when the molar ratio is in the above range. In addition, it is most preferable that the molar ratio of 2-phenyltoluene to 4-phenyltoluene is 0.77:0.23, and the eutectic point at this time is −10.75° C.

In addition, among the binary eutectic mixtures, it is preferable that the molar ratio of 3-phenyltoluene to 4-phenyltoluene is 0.6 to 0.999:0.4 to 0.001. The eutectic mixture of 3-phenyltoluene and 4-phenyltoluene maintains the liquid state at normal temperature when the molar ratio is in the above range. In addition, it is most preferable that the molar ratio of 3-phenyltoluene to 4-phenyltoluene is 0.74:0.26, and the eutectic point at this time is −7.45° C.

In addition, in the inventive concept, a hydrogen storage material can be prepared by a ternary system in which three materials are mixed.

A eutectic mixture of 2-phenyltoluene, 3-phenyltoluene, and 4-phenyltoluene has a molar ratio of a:b:c, where the following relation may be satisfied: a+b+c=1, a>0, b>0, and c<0.4.

In other words, the eutectic mixture of 2-phenyltoluene, 3-phenyltoluene and 4-phenyltoluene can maintain the liquid state at room temperature when 2-phenyltoluene and 3-phenyltoluene are appropriately mixed in a case in which the molar ratio of 4-phenyltoluene is less than 0.4.

In addition, it is most preferable to mix 2-phenyltoluene, 3-phenyltoluene, and 4-phenyltoluene at a molar ratio of 0.47:0.41:0.12, the melting point of the eutectic mixture may fall to a maximum of −28.85° C. when these are mixed at the above molar ratio. In addition, the hydrogen storage capacity thereof is 6.7 wt %, which is higher than that of the conventional liquid hydrogen storage material, and the eutectic mixture can reversibly store and release hydrogen.

The eutectic point of such a ternary system or binary system can be predicted by the thermodynamic relation. In other words, the eutectic point can be predicted by calculating the eutectic points of binary and ternary eutectic mixtures of 2-phenyltoluene, 3-phenyltoluene and 4-phenyltoluene using the thermodynamic relation.

The thermodynamic relation is as follows.

$$x_i^l = \exp \frac{\Delta H_i^{sl}}{RT_{mi}} \left( \frac{T - T_{mi}}{T} \right) \quad \text{Equation (2)}$$

Here, R is an ideal gas constant, $T_{mi}$ is the melting point of each pure material, and $\Delta H_i^{sl}$ is the heat of fusion of each pure material. The $\Delta H_i^{sl}$ value is estimated through the Marrero and Gani group-contribution method.

Figure 5:
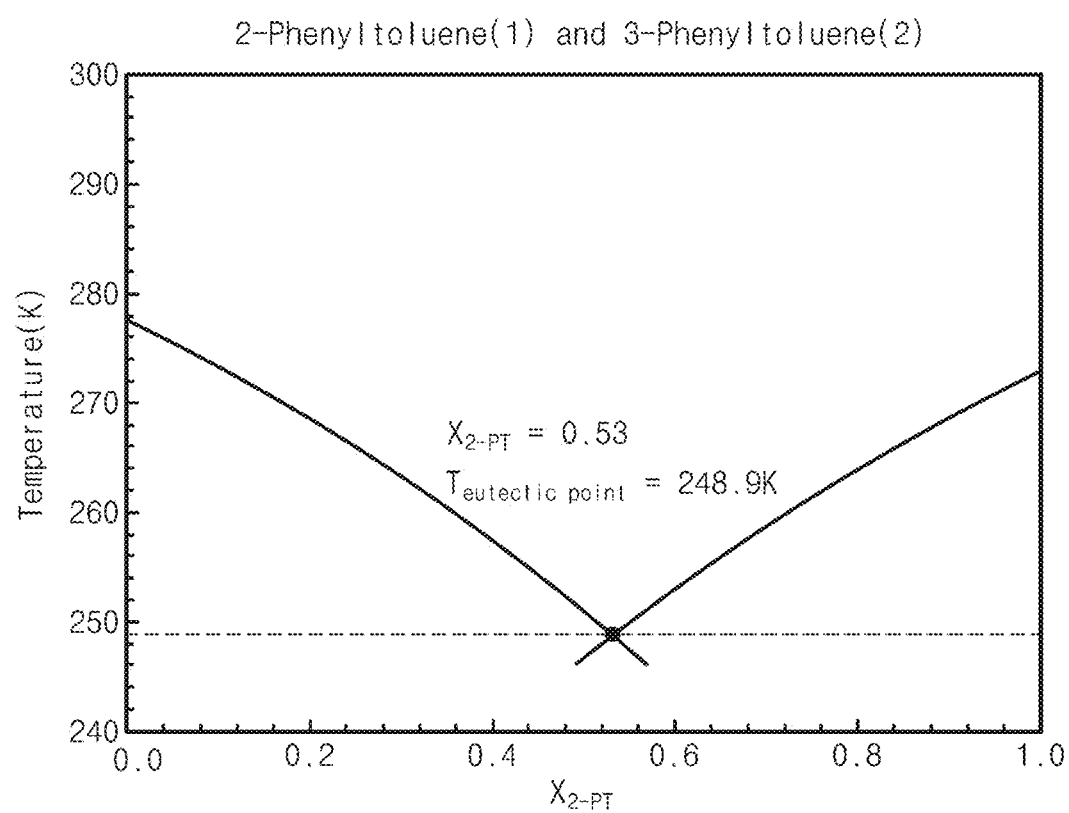
FIG. 5 illustrates the results for eutectic point prediction of a eutectic mixture of 2-phenyltoluene (2-PT) and 3-phenyltoluene (3-PT)

FIG. 5 illustrates the results for eutectic point prediction of a eutectic mixture of 2-phenyltoluene (2-PT) and 3-phenyltoluene (3-PT).

When 2-phenyltoluene (2-PT) and 3-phenyltoluene (3-PT) are mixed at a molar ratio of 0.53:0.47, it can be predicted the eutectic point of the eutectic mixture is −24.25° C. and the eutectic mixture is present as a liquid even at temperatures to be considerably lower than the melting points of the respective pure materials.

In addition, it can be seen that the eutectic mixture can maintain the liquid state at room temperature even though these are mixed in all molar ratio ranges.

Figure 6:
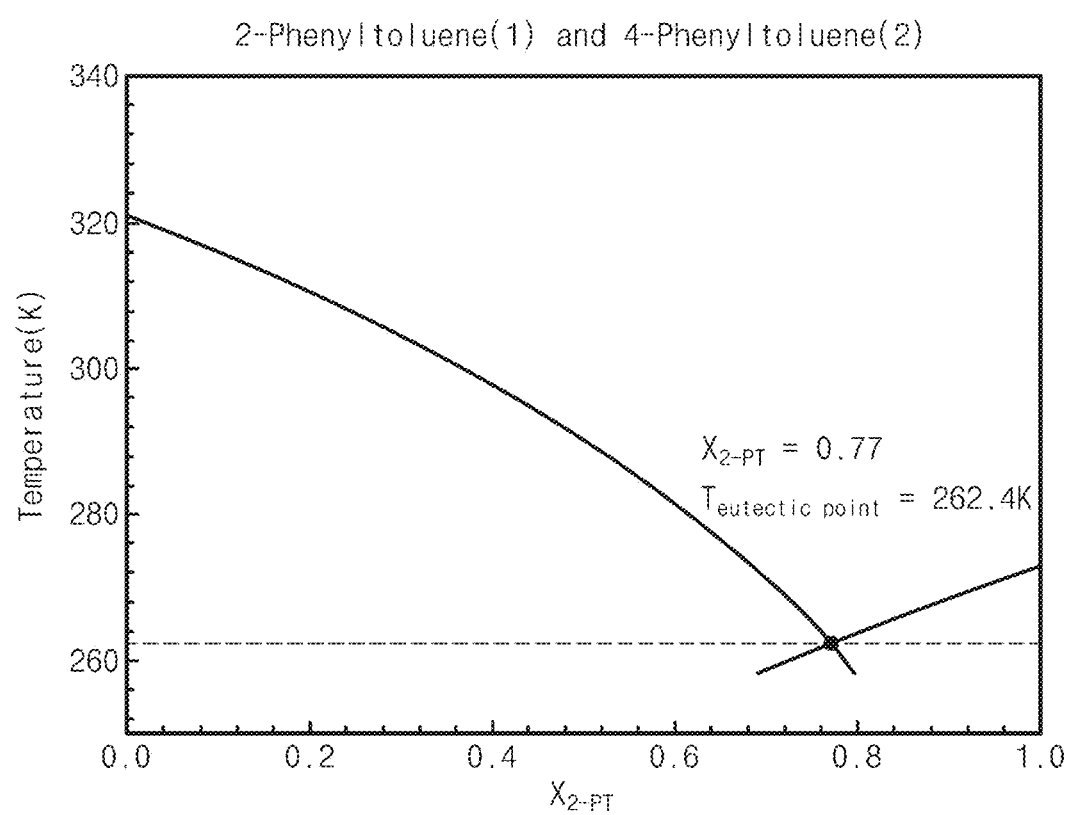
FIG. 6 illustrates the results for eutectic point prediction of a binary eutectic mixture containing 2-phenyltoluene (2-PT) and 4-phenyltoluene (4-PT)

FIG. 6 illustrates the results for eutectic point prediction of a binary eutectic mixture containing 2-phenyltoluene and 4-phenyltoluene.

Figure 7:
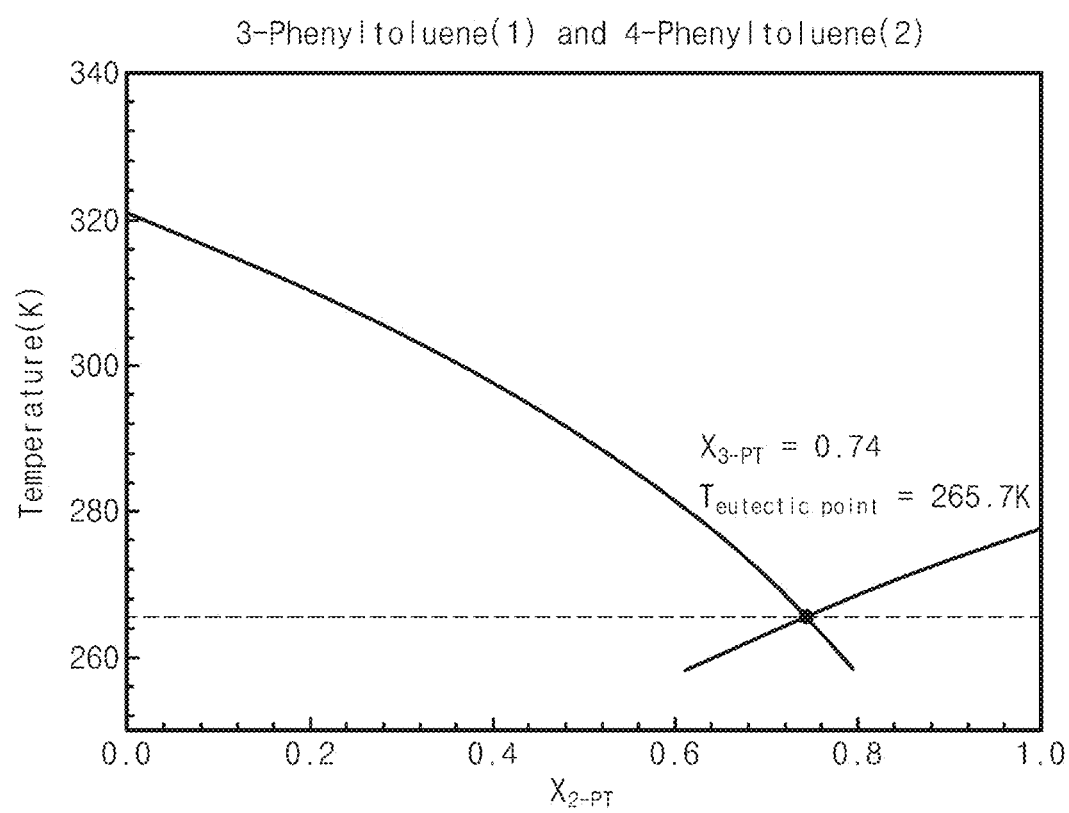
FIG. 7 illustrates the results for eutectic point prediction of a binary eutectic mixture containing 3-phenyltoluene (3-PT) and 4-phenyltoluene (4-PT)

In addition, FIG. 7 illustrates the results for eutectic point prediction of a binary eutectic mixture containing 3-phenyltoluene and 4-phenyltoluene.

The melting point of 4-phenyltoluene is from 44° C. to 47° C., but the melting point may be lowered when being mixed with 2-phenyltoluene or 3-phenyltoluene.

Referring to FIGS. 6 and 7, the eutectic mixture can be present as a liquid at room temperature when 2-phenyltoluene and 4-phenyltoluene or 3-phenyltoluene and 4-phenyltoluene are mixed and the molar ratio of 4-phenyltoluene is 0.4 or less.

In addition, as the lowest eutectic point, the eutectic point is −10.75° C. when the molar ratio of 2-phenyltoluene to 4-phenyltoluene is 0.77:0.23 and the eutectic point is −7.45° C. when the molar ratio of 3-phenyltoluene to 4-phenyltoluene is 0.74:0.26.

In addition, in the case of a ternary eutectic mixture in which three materials of 2-phenyltoluene (2-PT), 3-phenyltoluene (3-PT) and 4-phenyltoluene (4-PT) are mixed, the eutectic point can be generated at a temperature lower than the eutectic point of a eutectic mixture of 2-phenyltoluene and 3-phenyltoluene.

In addition, it is confirmed from the results illustrated in FIGS. 6 and 7 that a binary eutectic mixture containing 4-phenyltoluene maintains the liquid state at normal temperature when the molar ratio of 4-phenyltoluene (4-PT) is less than 0.4. Accordingly, it is preferable that the molar ratio of 4-phenyltoluene (4-PT) is less than 0.4 when the inventive concept is a ternary m-phenyltoluene (m=2, 3, 4) eutectic mixture.

Figure 8:
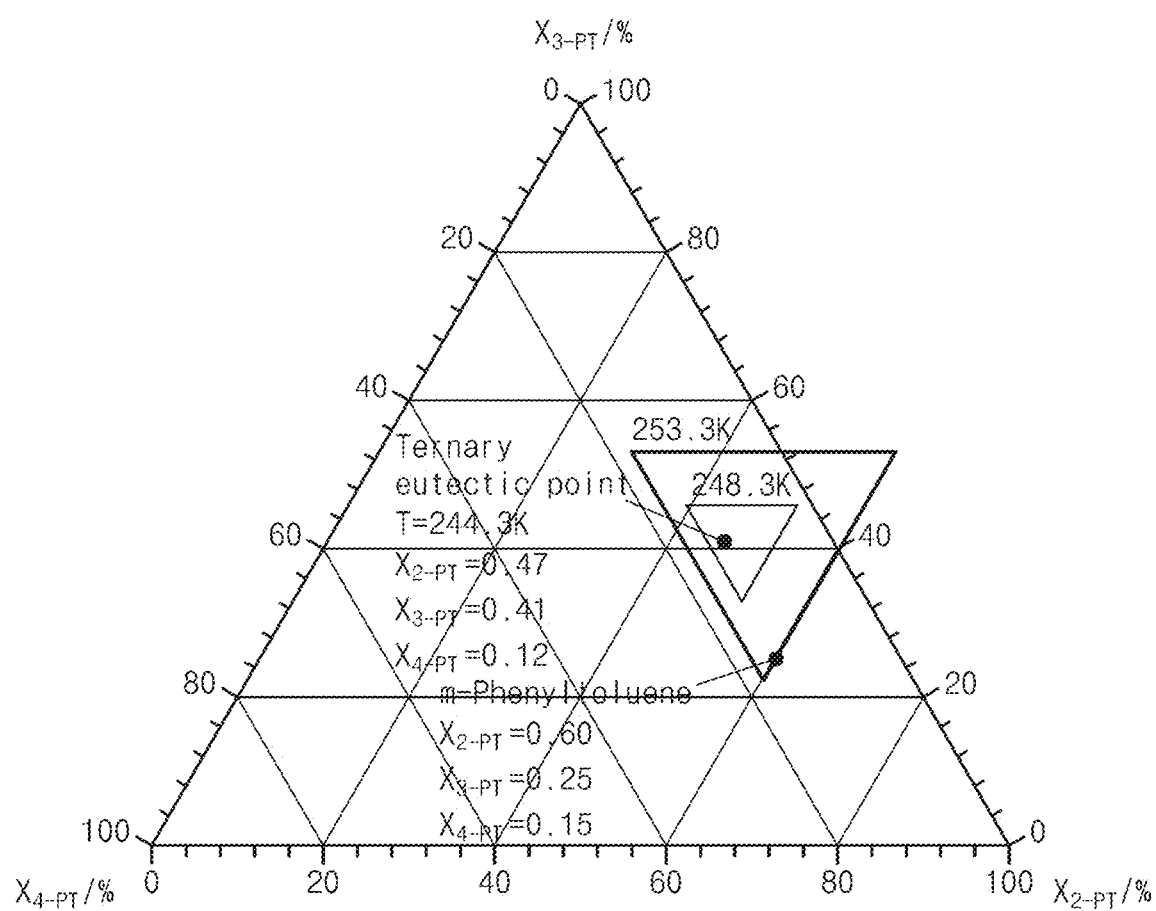
FIG. 8 illustrates the results for eutectic point prediction of a ternary m-phenyltoluene (m=2, 3, 4) eutectic mixture.

FIG. 8 illustrates the results for eutectic point prediction of a ternary m-phenyltoluene (m=2, 3, 4) eutectic mixture.

In FIG. 8, the green line indicates the solid-liquid phase equilibrium of eutectic mixtures at −19.85° C. In other words, a mixture having a molar composition inside the green line is present as a liquid at −19.85° C. In the same manner, the blue line indicates the solid-liquid phase equilibrium of eutectic mixtures at −24.85° C. A mixture having a molar composition inside the blue triangle is present as a liquid at −24.85° C. In addition, in case of mixing 2-phenyltoluene, 3-phenyltoluene and 4-phenyltoluene at a molar ratio of 0.47:0.41:0.12 (tertiary eutectic point), the solid-liquid phase equilibrium is obtained at −28.85° C. and it is confirmed that the eutectic mixture can be present as a liquid down to near this temperature.

Meanwhile, a catalyst is required for hydrogenation/dehydrogenation of a binary or ternary hydrogen storage material of m-phenyltoluene (m=2, 3, 4), and it is possible to use the same materials as the catalysts described above.

In other words, either of $Ru/Al_2O_3$ or Ru/C may be used as the hydrogenation catalyst to be used in the hydrogenation.

In addition, any one of Pd/C, $Pd/Al_2O_3$, Pt/C or $Pt/Al_2O_3$ is used as the dehydrogenation catalyst to be used in the dehydrogenation.

The hydrogenation reaction of a ternary eutectic mixture of m-phenyltoluene (m=2, 3, 4) may be conducted by using the apparatus illustrated in FIG. 1.

For example, for hydrogenation, a m-phenyltoluene (m=2, 3, 4) eutectic mixture (molar ratio of 2-PT:3-PT:4-PT=0.60:0.25:0.15) and the $Ru/Al_2O_3$ catalyst are introduced into a reactor and the reactor is purged with hydrogen for 30 minutes. The temperature of the reactor is raised to 150° C. by using a heating jacket, and the hydrogen pressure in the reactor is adjusted to 60 bar. Stirring is conducted by using the magnetic stirrer in the reactor during the hydrogenation reaction. The reaction is continuously conducted until the pressure does not change any more, and then the catalyst and the product are separated from each other through filtration. The product is subjected to $^1$H NMR analysis to judge whether the hydrogenation reaction has taken place.

In addition, the dehydrogenation is conducted by using the apparatus illustrated in FIG. 3. The Pt/C catalyst is introduced into the reactor and then the reactor is heated to the desired temperature by using a heating mantle while purging the reactor with nitrogen. When the temperature reaches the reaction temperature (200° C., 250° C.), nitrogen purge is stopped and the reactor and the oil burette are connected to each other and stabilized. The m-phenyltoluene (m=2, 3, 4) eutectic mixture hydrogenated is injected into the batch reactor by using a syringe. Hydrogen generated by the dehydrogenation reaction pushes the oil out of the oil burette and the mass of the oil pushed out is measured in real time by using a mass measuring apparatus. The mass of the oil pushed out is converted to the volume of hydrogen generated. When there is no more change in the mass measuring apparatus, the reaction is terminated and the structural change of the product is determined through $^1$H NMR analysis to judge whether the dehydrogenation reaction has taken place.

Figure 9:
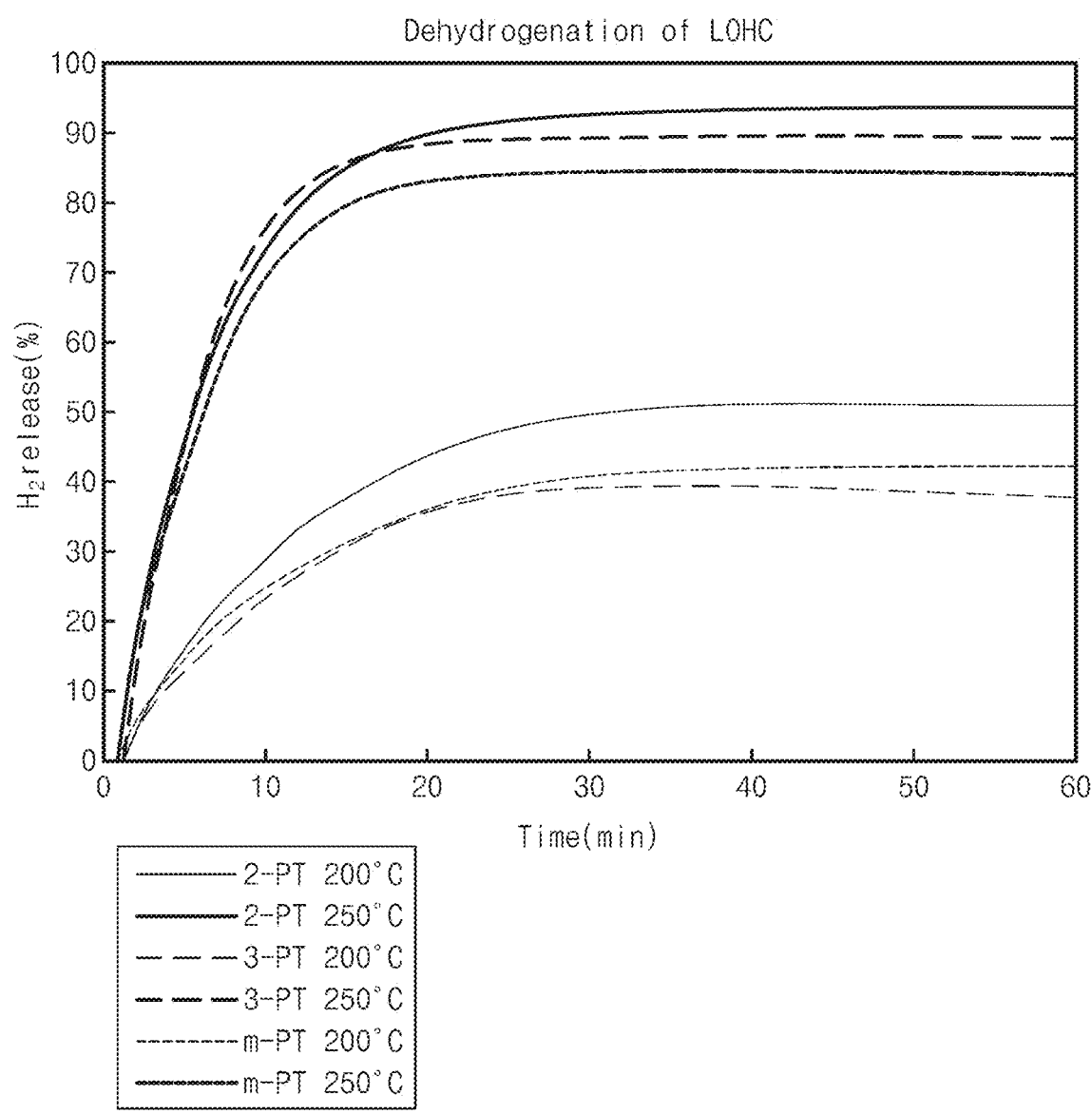
FIG. 9 illustrates the reaction conversion rate data obtained through the dehydrogenation reactions of hydrogenated 3-PT and 4-PT pure materials and a m-phenyltoluene (m=2, 3, 4) eutectic mixture (molar ratio of 2-PT:3-PT:4-PT=0.60:0.25:0.15) as a graph.

FIG. 9 illustrates the reaction conversion rate data obtained through the dehydrogenation reactions of hydrogenated 3-PT and 4-PT pure materials and a m-phenyltoluene (m=2, 3, 4) eutectic mixture (molar ratio of 2-PT:3-PT:4-PT=0.60:0.25:0.15) as a graph.

In the dehydrogenation experiment at 200° C., the reaction is completed within 30 minutes and the dehydrogenation conversion rate is from 40% to 50%. In the dehydrogenation experiment at 250° C., the reaction is completed within 20 minutes and the dehydrogenation conversion rate is from 85% to 95%. Hence, it is confirmed that the dehydrogenation reaction of hydrogenated m-phenyltoluene (m=2, 3) or a m-phenyltoluene (m=2, 3, 4) eutectic mixture is effective at a temperature of 250° C. or more. In addition, it is confirmed that dehydrogenation can proceed to a maximum of 95% at 250° C. to be relatively lower than a temperature of 300° C. or more that is the temperature for dehydrogenation reaction of conventional hydrocarbons.

Figure 10:
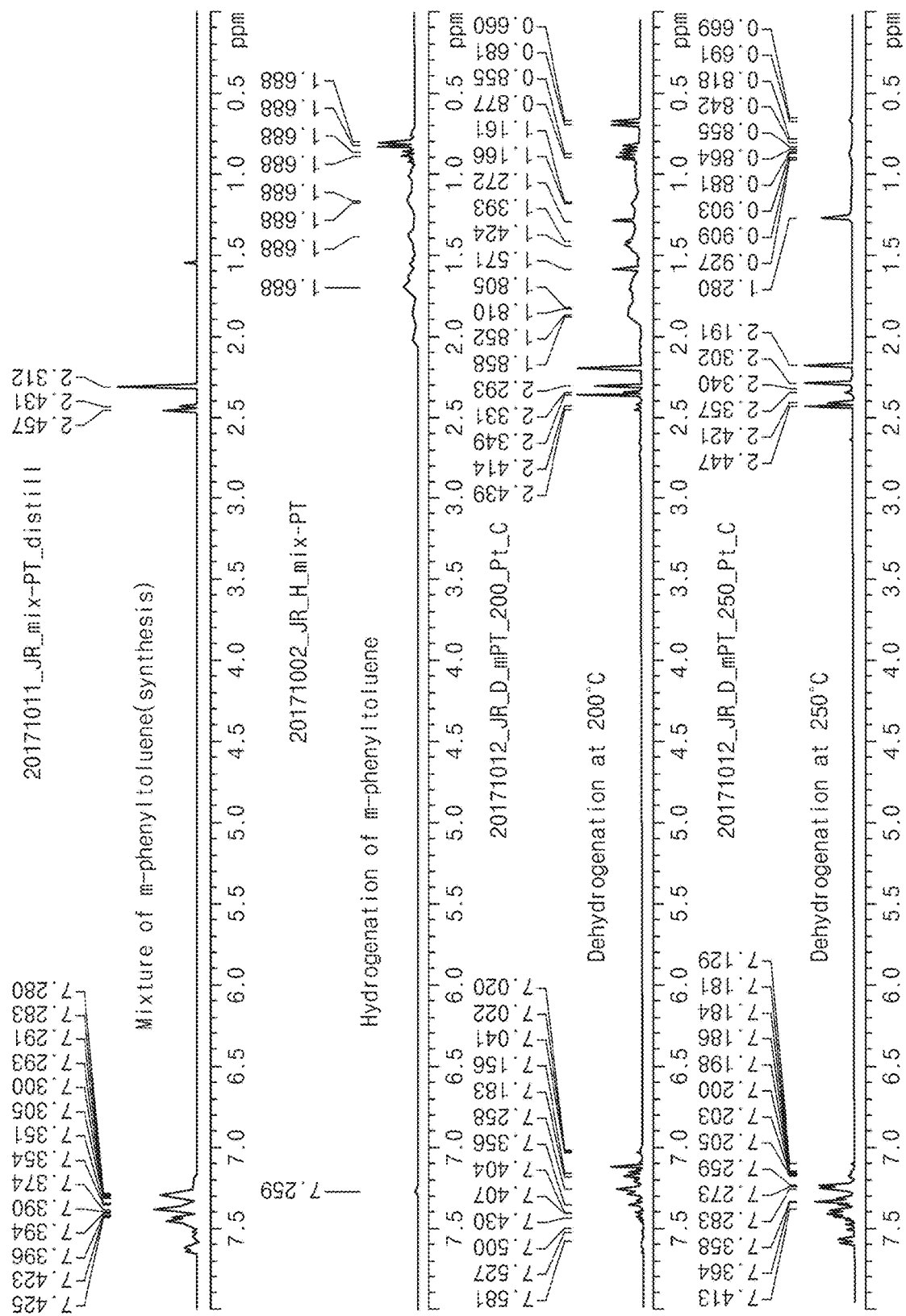
FIG. 10 illustrates the results for $^1$H NMR analysis of the structures of products obtained after the synthesis, hydrogenation reaction, and then dehydrogenation reaction of a m-phenyltoluene (m=2, 3, 4) eutectic mixture (molar ratio of 2-PT:3-PT:4-PT=0.60:0.25:0.15).

FIG. 10 illustrates the results for $^1$H NMR analysis of the structures of products obtained after the synthesis, hydrogenation reaction, and then dehydrogenation reaction of a m-phenyltoluene (m=2, 3, 4) eutectic mixture (molar ratio of 2-PT:3-PT:4-PT=0.60:0.25:0.15).

Referring to FIG. 10, the pure component ratio in the eutectic mixture after being synthesized can be judged by comparing the areas of the methyl group peaks with one another. It is confirmed that the methyl group peak of 2-phenyltoluene appears at 2.312 ppm, the methyl group peak of 3-phenyltoluene appears at 2.457 ppm, and the methyl group peak of 4-phenyltoluene appears at 2.431 ppm.

It is confirmed that the aromatic proton peaks at from 7 to 8 ppm all shift to the aliphatic proton peaks at from 0.5 to 2 ppm when the m-phenyltoluene (m=2, 3, 4) eutectic mixture synthesized is hydrogenated, and this means that the hydrogenation completely (100%) proceeds.

In addition, from the results for structural analysis conducted after the dehydrogenation reaction at 250° C., it is confirmed that the proton (H) peaks attributed to sp2-carbon of the aromatic ring appear again at between 7 and 8 ppm and, at the same time, the proton peaks attributed to the methyl group shift to 2.28 ppm of the original position, and it is confirmed that the dehydrogenation reaction qualitatively takes place through this.

Consequently, binary and ternary m-phenyltoluene (m=2, 3, 4) eutectic mixtures of the hydrogen storage material according to the inventive concept can maintain the liquid state at a low temperature, and particularly, a ternary eutectic mixture has a eutectic point at a maximum of −28.85° C.

In addition, it can be seen that the binary and ternary m-phenyltoluene (m=2, 3, 4) eutectic mixtures have a high hydrogen storage capacity of 6.7 wt % and can reversibly undergo the hydrogenation/dehydrogenation reactions. In addition, it can be seen that the dehydrogenation reaction of the hydrogenated m-phenyltoluene (m=2, 3, 4) eutectic mixtures of the inventive concept smoothly takes place even at a relatively low temperature of 250° C. while a high temperature of 300° C. or more is required for the dehydrogenation reaction of conventional hydrocarbon materials.

While the inventive concept has been described with reference to exemplary embodiments thereof, it will be apparent to those of ordinary skill in the art that various changes and modifications may be made thereto without departing from the spirit and scope of the inventive concept as set forth in the following claims.

What is claimed is:

1. A liquid hydrogen storage material comprising a ternary eutectic mixture of m-phenyltoluene (m=2, 3, 4), wherein the ternary eutectic mixture of m-phenyltoluene has a molar ratio of 2-phenyltolyene: 3-phenyltoluene: 4-phenyltoluene=a: b: c (where a+b+c=1, a>0, b>0, and 0<c<0.4.

2. A liquid hydrogen storage material comprising a binary eutectic mixture selected from the group consisting of 2-phenyltoluene and 3-phenyltoluene, 2-phenyltoluene and 4-phenyltoluene or 3-phenyltoluene and 4-phenyltoluene, wherein the eutectic mixture of 2-phenyltoluene and 3-phenyltoluene among the binary eutectic mixtures has a molar ratio of 2-phenyltoluene: 3-phenyltoluene=0.001 to 0.999: 0.999 to 0.001, the eutectic mixture of 2-phenyltoluene and 4-phenyltoluene among the binary eutectic mixtures has a molar ratio of 2-phenyltoluene: 4-phenyltoluene=0.6 to 0.999: 0.4 to 0.001 and the eutectic mixture of 3-phenyltoluene and 4-phenyltoluene among the binary eutectic mixtures has a molar ratio of 3-phenyltoluene: 4-phenyltoluene=0.6 to 0.999: 0.4 to 0.001.

* * * * *